(12) United States Patent
Park (10) Patent No.: US 9,687,028 B2
(45) Date of Patent: Jun. 27, 2017

(54) ELECTRONIC CIGARETTE

(71) Applicant: Sun Soon Park, Seoul (KR)

(72) Inventor: Sun Soon Park, Seoul (KR)

( * ) Notice: Subject to any disclaimer, the term of this patent is extended or adjusted under 35 U.S.C. 154(b) by 654 days.

(21) Appl. No.: 14/351,114

(22) PCT Filed: Apr. 2, 2013

(86) PCT No.: PCT/KR2013/002708
§ 371 (c)(1),
(2) Date: Apr. 10, 2014

(87) PCT Pub. No.: WO2013/151295
PCT Pub. Date: Oct. 10, 2013

(65) Prior Publication Data
US 2014/0261500 A1   Sep. 18, 2014

(30) Foreign Application Priority Data

Apr. 3, 2012   (KR) ........................ 10-2012-0034224

(51) Int. Cl.
| | | |
|---|---|---|
| A24F 13/00 | (2006.01) | |
| A24F 17/00 | (2006.01) | |
| A24F 25/00 | (2006.01) | |
| A24F 47/00 | (2006.01) | |
| A24B 15/16 | (2006.01) | |
| A61M 15/06 | (2006.01) | |
| A61M 11/04 | (2006.01) | |
| A61M 15/00 | (2006.01) | |

(52) U.S. Cl.
CPC ............ *A24F 47/008* (2013.01); *A24B 15/16* (2013.01); *A24B 15/167* (2016.11); *A61M 11/042* (2014.02); *A61M 15/002* (2014.02); *A61M 15/06* (2013.01); *A61M 2205/3653* (2013.01); *A61M 2205/8206* (2013.01)

(58) Field of Classification Search
None
See application file for complete search history.

(56) References Cited

U.S. PATENT DOCUMENTS

2011/0303231 A1* 12/2011 Li ........................ A24F 47/008
131/329

FOREIGN PATENT DOCUMENTS

| KR | 10-1008882 | 2/2007 |
|---|---|---|
| KR | 10-0933516 | 12/2009 |
| KR | 20-2010-0002123 | 3/2010 |
| KR | 10-1011453 | 1/2011 |
| KR | 20-0455259 | 8/2011 |
| KR | 10-2012-0002555 | 1/2012 |

OTHER PUBLICATIONS

International Search Report issued in PCT/KR2013/002708, mailed Jun. 18, 2013.

* cited by examiner

*Primary Examiner* — Michael H Wilson
*Assistant Examiner* — Phu Nguyen
(74) *Attorney, Agent, or Firm* — Norton Rose Fulbright US LLP

(57) ABSTRACT

Disclosed is an electronic cigarette including a suction part, an atomizer structure body, a liquid storing part, a main body including a switch, and a battery. In this case, the atomizer structure body includes a flexible nonflammable metal net, an absorption part configured to absorb a condensed liquid, a returning part configured to return and supply the condensed liquid, a crucible, and a liquid charging cap.

2 Claims, 8 Drawing Sheets

ELECTRONIC CIGARETTE

CROSS-REFERENCE TO RELATED APPLICATION

This application is a national phase application under 35 U.S.C. §371 of International Patent Application No. PCT/KR2013/002708 filed Apr. 2, 2013, which claims priority to and the benefit of Korean Patent Application No. 10-2002-0034224, filed on Apr. 3, 2012. The disclosures of the referenced applications are incorporated herein by reference in their entireties.

BACKGROUND

1. Field of the Invention

The present invention relates to an electronic cigarette which includes a suction part, an atomizer structure body, a liquid storing part, a main body including a switch, and a battery, wherein the atomizer structure body includes a flexible nonflammable metal net, an absorption part which may absorb a condensed liquid, a returning part which returns and supplies the condensed liquid, a crucible, and a liquid charging cap.

2. Discussion of Related Art

An electronic cigarette is an electronic device which heats and atomizes liquefied nicotine with an electric heater so that a user may suck in the atomized vapor.

Figure 1:
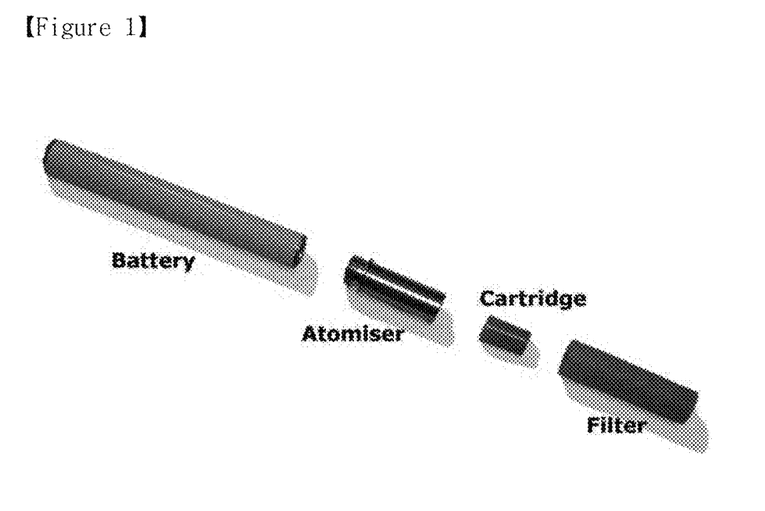
FIG. 1 is a view illustrating a general electronic cigarette.

As illustrated in FIG. 1, the electronic cigarette generally includes an electronic cigarette main body, a battery, an atomizer, and a cartridge. Here, the cartridge serves to store a liquid of the electronic cigarette, and the atomizer is connected with the cartridge and serves to heat and atomize the liquid in the cartridge.

Generally, a heating part of the atomizer uses a nichrome wire as a coil of an electric heater to produce heat well. A supplying body configured to directly supply the liquid to the heating part is formed of glass fiber and provided in a thread shape.

Meanwhile, the cartridge stores the liquid, and the liquid may be stored in a tank type or a storing container type, like storing ink in a pen, or may be stored in a member such as cotton. However, in this storing manner of the liquid, there is a problem that the liquid in the container is rapidly exhausted, and thus the liquid has to be frequently charged. Further, since it is difficult to properly limit an amount of sucking liquid, a user may suck in an excessive amount at a time.

Most of the conventional electronic cigarettes use a liquid supplying device using the force of gravity, and thus a liquid supplying part is structurally disposed above the heating part. Therefore, when the user uses the electronic cigarette, the liquid supplying part has to be disposed above the heating part in order for the liquid to be smoothly supplied. However, such a posture is very inconvenient.

Meanwhile, in case of the conventional electronic cigarettes, the glass fiber is used as a liquid supplying medium, but the glass fiber is easily broken and thus has very low durability, and also the broken chips of the glass fiber may be sucked into a user's body. Further, when the glass fiber is directly in contact with the electric heating wire and vaporizes the liquid, combustion occurs at a moment when the liquid is in contact with an overheated electric heating wire, and at this time, a burnt taste is generated and thus a taste of the electronic cigarette is deteriorated, and also a toxic substance may be generated. Furthermore, burnt residues generated when the liquid is combusted by the overheated electric heating wire are accumulated at the glass fiber, and durability of the atomizer is considerably reduced, and thus the atomizer itself including the atomizer structure body and the liquid supplying device has to be replaced with new one, whereby an economical loss is considerable.

Further, in case of the conventional electronic cigarettes, the liquid incompletely atomized by a flash heating manner occurring when the liquid supplied through the glass fiber thread is directly in contact with the heated electric wire may easily form condensation on a wall of the equipment while being sucked into a user's mouth through the atomizer and a pipe, and thus the equipment may be overheated, and also atomization efficiency is lowered. However, since there are no separate devices for enhancing the atomization efficiency and returning the condensed liquid, a secondary problem such as a leak may be caused. The leaked liquid in itself is a waste, and also if the leaked liquid is in contact with a printed circuit board (PCB) (a current PCB is manufactured to have a separate integral battery regardless of an auto or manual type, and thus has inconvenience and burden of expenses when the separate battery has to be replaced according to a power source operating manner), a defect of the PCB may occur and this causes a defect in whole batteries.

Further, the glass fiber is recently classified as a '2B grade' cancer-causing material by International Agency for Research on Cancer (IARC) of WHO, and causes controversy of harmfulness.

SUMMARY OF THE INVENTION

The present invention is directed to a novel electronic cigarette structure body which may solve a problem in using glass fiber as a liquid supplying medium of an atomizer used in a conventional electronic cigarette, and thus in which liquid is smoothly supplied without force of gravity and internal temperature is properly maintained by a crucible, thereby enabling complete and uniform atomization of the liquid and solving problems, such as a leak of the liquid occurring in a conventional electronic cigarette which has a simple vapor generating device limited only to heat the liquid by a heater, using a separate functional device, and also an atomization enhancer for enhancing atomization efficiency and a battery body combined with a large capacity liquid storing and supplying device and including a replaceable multifunctional PCB are provided, thereby revolutionarily improving convenience of use.

According to an aspect of the present invention, there is provided an electronic cigarette including a suction part, an atomizer structure body, a liquid storing part, a main body including a switch, and a battery, wherein the atomizer structure body includes a flexible nonflammable metal net, an absorption part configured to absorb a condensed liquid, a returning part configured to return and supply the condensed liquid, a crucible, a liquid charging cap, an atomization enhancer, and an air controlling part, and the flexible nonflammable metal net is rolled up in a scroll shape and disposed so that a part of the rolled flexible nonflammable metal net is inserted into the liquid storing part in an axial direction parallel with a lengthwise direction of the scroll shape, and a power source terminal for supplying power is formed at the opposite side of the inserted portion of the flexible nonflammable metal net inserted into the liquid storing part, and the crucible is installed to enclose the power source terminal of the flexible nonflammable metal net, and the liquid charging cap is installed in the liquid storing part to enclose the flexible nonflammable metal net, and an opening configured to enable the liquid to be introduced is formed at a center of the liquid charging cap, and the atomization enhancer has a cylindrical shape of which one surface is blocked, and is installed to enclose an upper portion of the crucible, and air holes are formed along an outer circumference of the cylindrical shape so that air is introduced therethrough and mixed with high temperature vapor atomized and discharged from the crucible, and a discharging hole is formed in the blocked surface, and the air controlling part has a pair of ring shapes and is installed to enclose the atomization enhancer and a lower portion of the crucible in the suction part, and openings are formed along an outer circumference of the ring shape, and the ring-shaped air controlling part is rotatable about a center of the ring so that the crucible and the air holes formed along the outer circumference of the cylindrical shape of the atomization enhancer are in communication with each other through the openings formed along the outer circumference of the ring shape and the openings formed in the suction part, and the main body including the switch and the battery are detachably coupled with each other, and in this case, a manual mode, an automatic mode, and a continuously supplying mode are switched according to an operation of the switch, and the liquid supplied through the flexible nonflammable metal net to a heating part to which the power source terminal is installed is atomized by heat generated when power is supplied.

In this case, the absorption part configured to absorb the condensed liquid may include a funnel-shaped net and a net type tube which absorb the condensed liquid, and the returning part configured to return and supply the condensed liquid may include a flat net and a tube which supply the liquid absorbed by the absorption part to the heating part.

BRIEF DESCRIPTION OF THE DRAWINGS

The above and other objects, features, and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Embodiments of the present invention will be described in detail below with reference to the accompanying drawings. The same reference numerals are given to the same or corresponding parts, and the description thereof will not be repeated. In the specification, various exemplary embodiments are provided to explain the present invention. However, it is apparent that these exemplary embodiments can be embodied without these particular explanations. In these exemplary embodiments, the well-known structures and devices are provided in a block diagram in order to facilitate the explanation of the embodiments.

The below description provides simplified explanation of one or more exemplary embodiments and thus provides basic understanding of the embodiments of the present invention. This section is not the comprehensive concept of possible embodiments, and also does not intent to distinguish a core element from all elements or to cover all possible variations, alternatives, or every aspects of the present invention. The sole purpose thereof is to provide one or more simplified concepts of the embodiments as introduction of the detailed description.

FIG. 1 is a view illustrating a general electronic cigarette. A general structure of an electronic cigarette basically includes an atomizer, a cartridge configured to store a liquid, a filter, and a battery. The atomizer is a part which is connected with the cartridge to heat and atomize the liquid of the cartridge. Generally, a heating part of the atomizer uses a nichrome wire as a coil of an electric heater to produce heat well, and a supplying body configured to directly supply the liquid to the heating part is formed of glass fiber and provided in a thread shape.

Unlike the general electronic cigarette, the present invention discloses a revolutionarily improved electronic cigarette structure body which uses a nonflammable metal net (if necessary, a nonflammable net) instead of the glass fiber and also provides a new functional body for solving problems in the conventional electronic cigarette structure body.

In case of using the nonflammable metal net, the metal net itself also serves as a heating part. In case of using the nonflammable net, the net itself does not serve as the heating part, and a separate heating part is provided.

Figure 2:
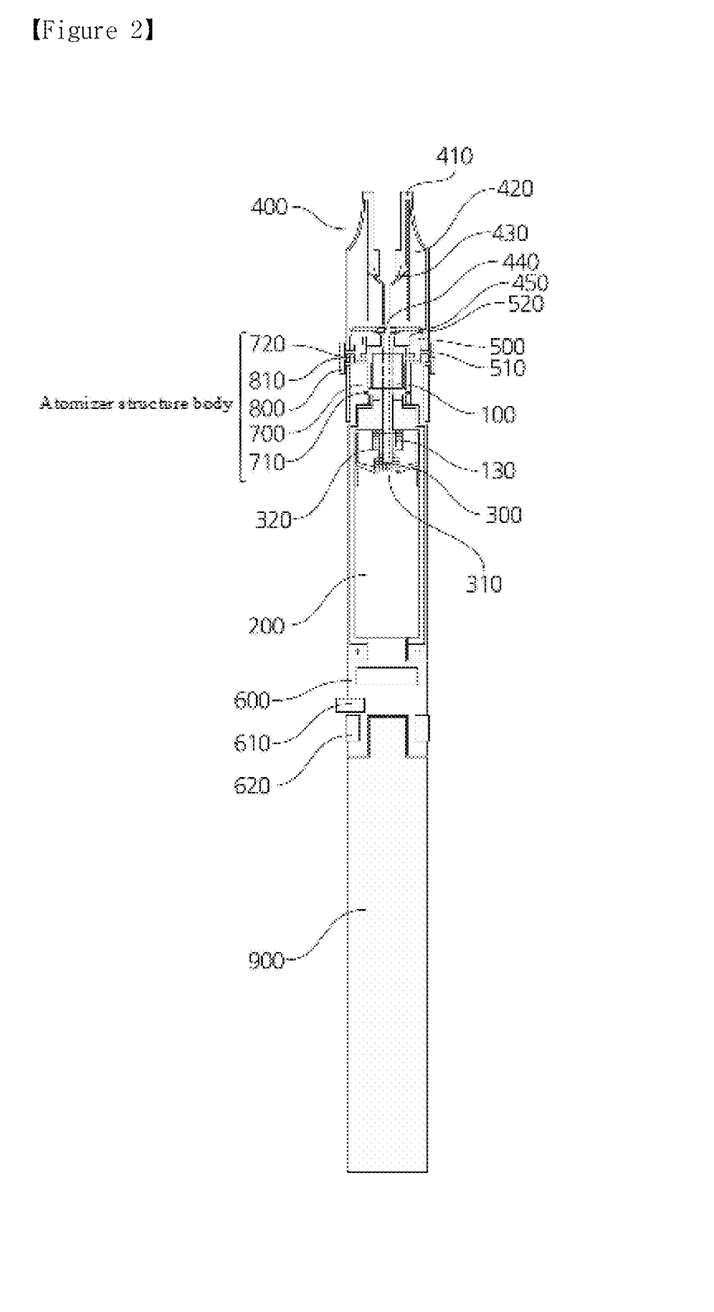
FIG. 2 is a cross-sectional view of a structure of an electronic cigarette in accordance with one embodiment of the present invention.
Figure 3:
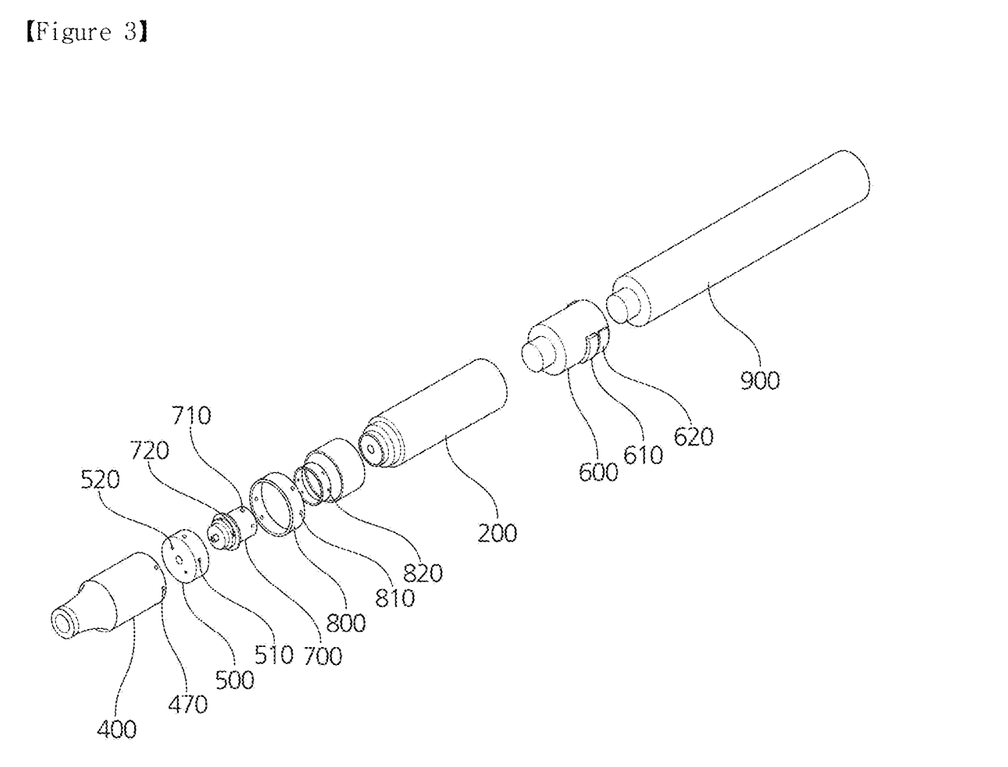
FIG. 3 is an exploded perspective view of the electronic cigarette in accordance with one embodiment of the present invention.
Figure 4:
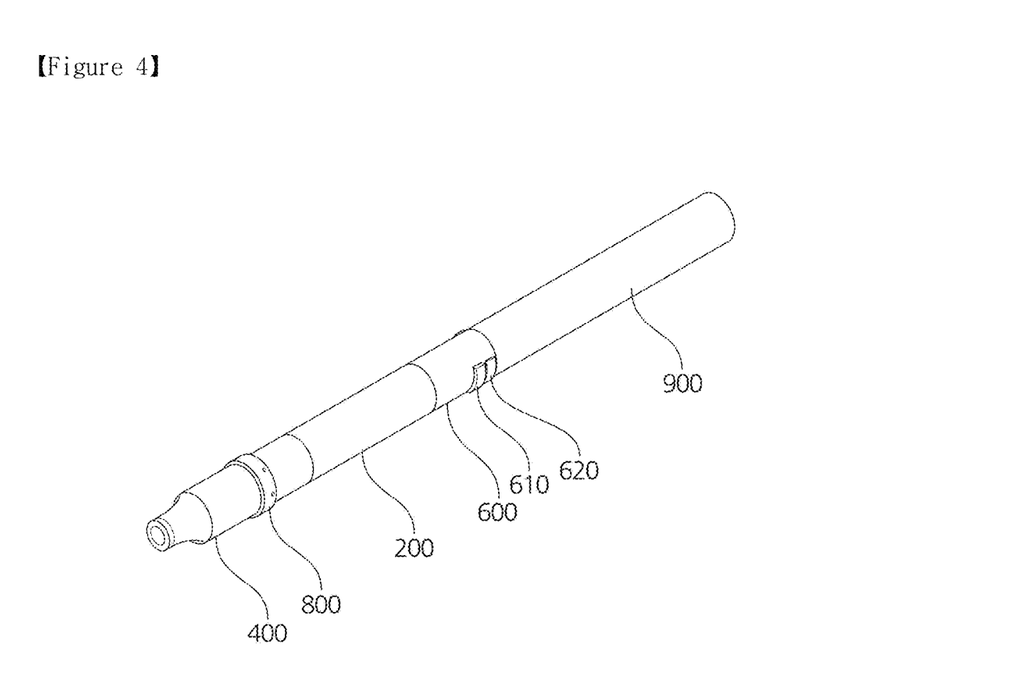
FIG. 4 is an assembled perspective view of the electronic cigarette in accordance with one embodiment of the present invention.

FIG. 2 is a cross-sectional view of a structure of an electronic cigarette in accordance with one embodiment of the present invention, FIG. 3 is an exploded perspective view thereof, and FIG. 4 is an assembled perspective view thereof. As illustrated in FIG. 2, a structure of an electronic cigarette in accordance with one embodiment of the present invention includes an atomizer structure body including a nonflammable net 100 or the like, a liquid storing part 200, a suction part 400 through which a user sucks in atomized vapor, a main body 600 including a switch, and a battery 900.

The atomizer structure body includes a flexible nonflammable metal net 100, an absorption part 420, 430 configured to absorb a condensed liquid, a returning part 440, 450 configured to return and supply the condensed liquid, a crucible 700, a liquid charging cap 300, an atomization enhancer 500, and an air controlling part 800.

The flexible nonflammable metal net 100 is rolled up in a scroll shape and disposed so that a part of the rolled flexible nonflammable metal net 100 is inserted into the liquid storing part 200 in an axial direction parallel with a lengthwise direction of the scroll shape.

Figure 5A:
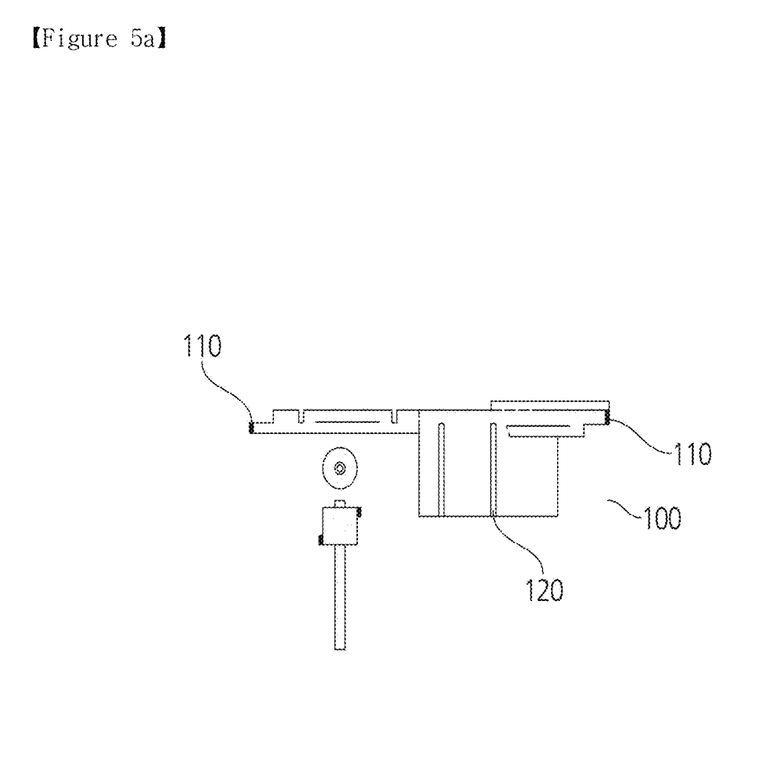
FIGS. 5A and 5B are a side view and a plan view respectively illustrating each state in which a nonflammable metal net is unfolded and rolled up in a scroll shape.
Figure 5B:
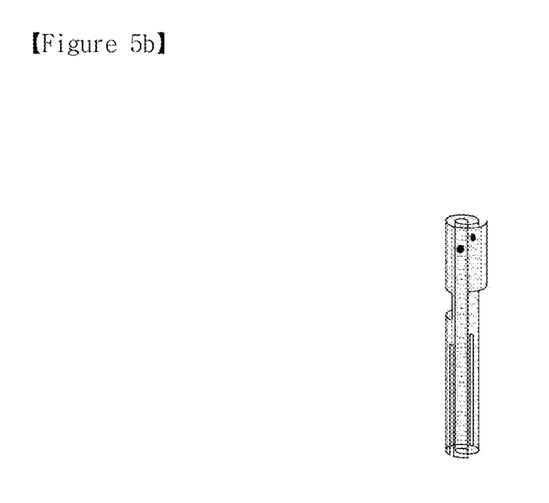

An unfolded state of the flexible nonflammable metal net 100 is illustrated in FIG. 5. FIG. 5 illustrates a side view and a plan view respectively illustrating each state in which the flexible nonflammable metal net is unfolded, and folded in half and rolled up in a scroll shape. As illustrated in FIG. 5, a power source terminal 110 is formed at an opposite side of an inserted portion of the flexible nonflammable metal net inserted into the liquid storing part.

The nonflammable metal net serves to hold and continuously supply the liquid, and simultaneously serves as the heating part which receives power and atomizes the liquid. Therefore, the nonflammable metal net is formed of a conductive metallic material. Further, the nonflammable metal net has flexibility to be used in a state of being rolled up in the scroll shape and inserted into the electronic cigarette. For example, the nonflammable metal net may include a stainless net, a nichrome wire net, an aluminum net, a tungsten net, and the like.

As illustrated in the unfolded state (before being rolled up in the scroll shape) of FIG. 5, the nonflammable metal net 100 includes the power source terminal 110 and an air passage 120.

The nonflammable metal net has a net structure and is rolled up in the scroll shape, and a part of the nonflammable metal net is inserted into the liquid storing part in the axial direction parallel with the lengthwise direction of the scroll shape. Thus, the nonflammable metal net holds the liquid in the liquid storing part and then continuously supplies the liquid to the heating part.

In this case, as described above, the nonflammable metal net also serves as the heating part. As illustrated in FIG. 5, in order to serve as the heating part, the nonflammable metal net has the power source terminal 110 to which two power supplying lines are connected. Since the power supplying lines are connected to the power source terminal 110, the nonflammable metal net receives power, when the liquid is supplied between two points of the nonflammable metal net 100, and heats and atomizes the liquid. The user of the electronic cigarette sucks in the atomized vapor through the suction part 400.

The air passage 120 serves as a passage configured to enable the liquid to be smoothly supplied through the net, and thus the liquid may be further rapidly and smoothly supplied by the air passage 120. One or more air passages 120 may be installed, and the number of the air passages 120 is not particularly limited.

Meanwhile, a separate built-in heating part may be installed. In this case, the nonflammable net may include any net structure formed of a nonflammable material. Since the separate built-in heating part is provided, the nonflammable net does not need to be formed of a metallic material.

An electric heating wire is formed to connect two points of the power source terminal 110, and receives the power through a power supplying wire and generates heat. The heating wire may generally use a nichrome wire, but is not limited thereto. The heating wire may be formed of any flexible conductive material.

In the present invention, the scroll-shaped flexible nonflammable net may be inserted into the crucible together with a jack and also separated therefrom. Therefore, the user may easily remove the flexible nonflammable net from the atomizer structure body of the electronic cigarette and then may replace or clean the flexible nonflammable net. Further, the power source terminal of the nonflammable net may be fixed to the jack located at an upper end of the crucible, and the crucible may be inserted and installed into a lower end of the liquid storing part 200 to receive the power, such that the power source terminal is integrally formed with the crucible, and thus the atomizer may be easily replaced.

In this case, as illustrated in FIG. 2, (+) and (−) portions indicated next above the main body 600 connected with (+) and (−) terminals of the battery are connected to a lower portion of the crucible 700 through wires, and as illustrated in FIG. 2, the (+) and (−) portions are indicated at a lower portion thereof. In the crucible, portions which are respectively conductively connected with the (+) and (−) portions are provided, and the power source terminal 110 of the flexible nonflammable net is inserted into the portions together with the jack to receive the power.

Figure 6:
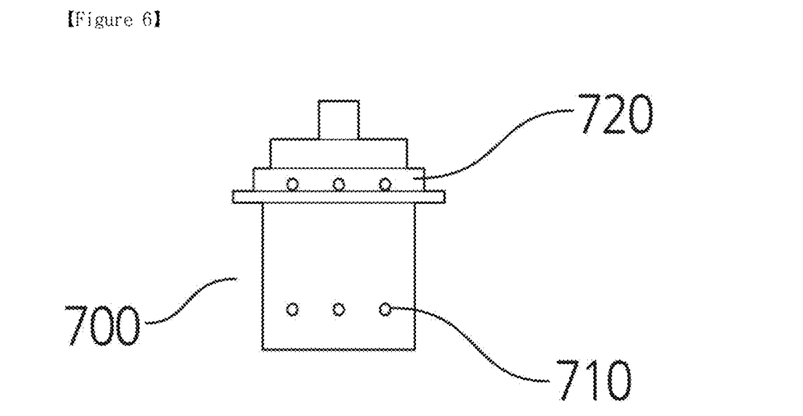
FIG. 6 is a side view of a crucible in accordance with one embodiment of the present invention.

The crucible 700 is installed to enclose the portion at which the power source terminal of the flexible nonflammable metal net is formed (referring to FIG. 2). That is, the crucible 700 is installed to enclose the opposite portion of the inserted portion of the flexible nonflammable metal net inserted into the liquid storing part. The crucible 700 has a cylindrical shape, and a jack type terminal for connecting the power source is installed therein. The crucible 700 includes an air introduction port 710 and a vapor discharging port 720 (referring to FIG. 6). Air is introduced through the air introduction port, and the atomized vapor in the crucible flows to the atomization enhancer through the vapor discharging port 720.

The crucible 700 is formed of a ceramic material, and may be formed of a low density absorbable ceramic material. The crucible 700 is installed to enclose the flexible nonflammable metal net (referring to FIG. 2), and thus when the heat is generated, the crucible 700 serves to constantly maintain internal temperature of the heating part and to prevent unsaturated boiling of the liquid, thereby enabling a double boiling function.

The ceramic crucible may rapidly absorb high temperature and also may uniformly radiate heat. Due to such a property, the ceramic crucible may rapidly absorb the heat of the heating part (the high temperature electric heating wire) which instantaneously generates the heat, reduce the temperature and thus prevent combustion of the liquid, and also may uniformly radiate the absorbed heat to the excessively supplied liquid and thus double-boils the liquid. Further, low cured ceramic may absorb the liquid according to a cured degree of the ceramic and thus atomize the liquid in the ceramic, thereby maximally performing the double boiling effect.

Figure 7:
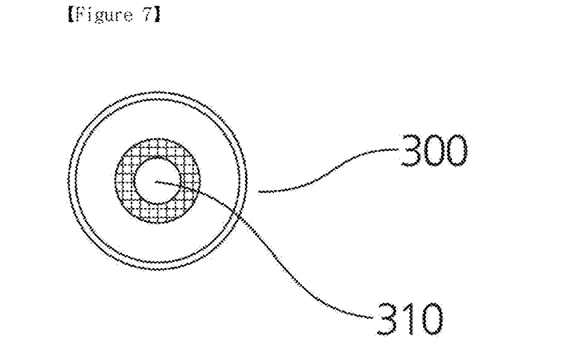
FIG. 7 is a plan view of a liquid charging cap in accordance with one embodiment of the present invention.

The liquid charging cap 300 is installed to enclose the flexible nonflammable metal net in the liquid storing part (FIG. 2), and an opening 310 and a liquid guiding net 320 are formed at a central portion of the liquid charging cap 300 to enable introduction of the liquid (referring to FIG. 7).

The liquid charging cap 300 serves to prevent an outflow of the liquid, charge the liquid, and thus always uniformly supply the liquid to an absorbing portion of a liquid supplying net. That is, the liquid charging cap 300 serves to allow the introduction of the liquid guided by the liquid guiding net 320 through the opening 310 but limit the outflow of the liquid. This function serves to enable the liquid to be easily supplied to the heating part, to enable the liquid storing part 200 to have a large capacity, and thus to revolutionarily improve inconvenience of frequently charging the liquid, and also serves as a safety device which limits an amount of the liquid sucked at a time to an amount of the liquid introduced into the liquid charging cap 300 (thus a desired time is required to recharge the liquid) and thus prevents unconsciously excessive suction of the electronic cigarette.

The atomization enhancer 500 has a cylindrical shape of which one surface is blocked, and is installed to enclose an upper portion of the crucible (referring to FIG. 2). Air holes (510) are formed along an outer circumference of the cylindrical shape so that air is introduced therethrough, and a discharging hole 520 is formed in the blocked surface thereof to discharge the atomized vapor (referring to FIG. 8).

Figure 8:
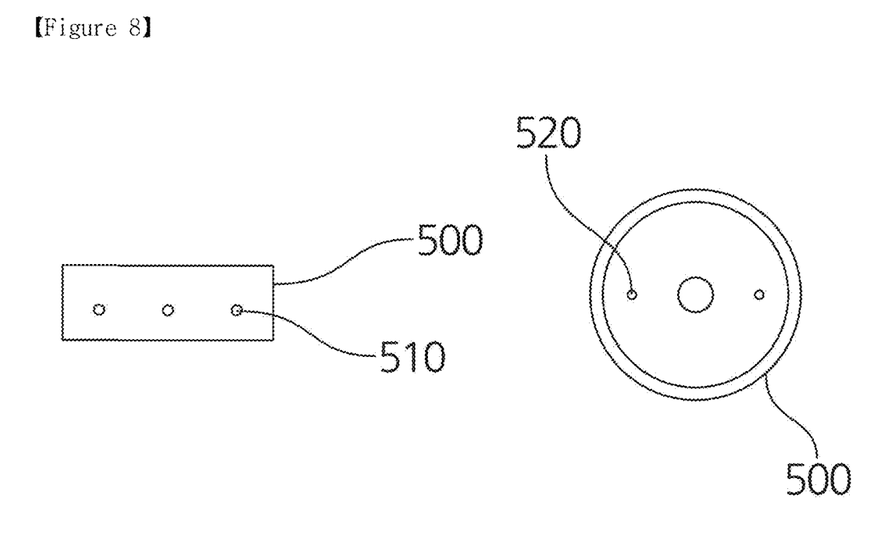
FIG. 8 is a plan view of an atomization enhancer in accordance with one embodiment of the present invention.

The atomization enhancer 500 is a cap-shaped component formed of a silicon material, which serves to mix the vapor discharged from the crucible and newly introduced air. The air is introduced through the air holes 510, and the discharged vapor is mixed with the introduced air through the discharging hole 520 to reduce temperature of the atomized vapor, to prevent overheat of peripheral components and to discharge the atomized vapor enhanced by a smoke phenomenon.

The air controlling part 800 is configured with two ring shapes and installed to enclose the atomization enhancer and a lower end of the crucible in the suction part 400 (referring to FIG. 2), and openings 810 and 820 are formed along an outer circumference of each of the ring shapes. The openings 810 and 820, the air holes 510 formed at the outer circumference of the cylindrical shape of the atomization enhancer, and the air introduction port 710 of the crucible 700 are in communication with each other. Therefore, external air may be introduced into the crucible and the atomization enhancer. In this case, to control an amount of the introduced air, the ring-shaped air controlling part 800 may be rotated about a center of the ring, and the openings 810 and 820 of the air controlling part 800 and each air hole of the suction part are crossed with each other so that a size of each air hole is controlled, and thus the amount of the introduced air may be controlled.

The absorption part 420, 430 which may absorb a condensed liquid includes a funnel net 430 and a net type tube 420 which may absorb the condensed liquid. Incompletely atomized vapor of the atomized vapor is condensed by the funnel net 430 and the net type tube 420 installed at a condensed liquid absorbing frame 410 and then supplied to the returning part 440, 450.

The returning part 440, 450 which returns and supplies the condensed liquid includes a returning net 450 and a returning tube 440 which may supply the liquid absorbed by the absorption part 420, 430 to the heating part.

The returning net 450 serves to return the condensed liquid to the heating part, and the returning tube 440 serves to supply the liquid absorbed by the returning net 450 to the heating part.

An atomized vapor discharging hole and net fixing caps may be formed at the returning part 440, 450.

Meanwhile, the main body 600 includes the switch of the electronic cigarette. In this case, a printed circuit board (PCB) as an electronic circuit is installed with the switch. So far, the PCBs of all batteries are formed integrally with the batteries. In this case, when the battery is defective, the defect is caused by a defect of the PCB. Therefore, the battery which is not defective has to be also replaced due to the defect of the PCB. However, to solve the problem, the present invention is designed so that the PCB including the switch is separately located at a battery coupling part. Therefore, when the battery is defective, only the battery coupling part may be replaced.

The PCB of the main body is designed (1) to be operated as a manual switch when using the electronic cigarette by pressing a power switch 610, (2) to be operated so that the power is automatically supplied when using the electronic cigarette by continuously pressing the switch twice at 1 second intervals, and (3) to be operated so that the power is continuously supplied when using the electronic cigarette by continuously pressing the switch three times at 1 second intervals.

Accordingly, the user may freely use the electronic cigarette in a desired power supplying manner, and thus it is not necessary to separately provide the batteries according to its application.

Further, according to one embodiment of the present invention, the main body and the battery are detachably coupled with each other, like the jack. Therefore, replacement of the battery is very easy. As illustrated in FIG. 3, in this coupling manner, a portion connected with the battery body protrudes partially, and this protruding portion is inserted into a complementary concave portion of the main body to be firmly coupled. Electrodes are formed at the protruding portion and the concave portion so that the power may be supplied at the same time of the insertion of the protruding portion.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An electronic cigarette comprising a suction part, an atomizer structure body, a liquid storing part, a main body including a switch, and a battery,
    wherein the atomizer structure body comprises a flexible nonflammable metal net, and
    the flexible nonflammable metal net is rolled up in a scroll shape and disposed so that a part of the rolled flexible nonflammable metal net is inserted into the liquid storing part in an axial direction parallel with a lengthwise direction of the scroll shape, and
    the flexible nonflammable metal net holds a liquid of the liquid storing part through the net and supplies the liquid continuously, and
    a power supplying line configured to supply power is connected to an opposite side of an inserted portion of the flexible nonflammable metal net so that the flexible nonflammable metal net generates heat and atomizes the liquid.

2. The electronic cigarette of claim 1, wherein the atomizer structure body further comprises a liquid charging cap, and the liquid charging cap is installed in the liquid storing part to enclose the flexible nonflammable metal net, and an opening configured to enable the liquid to be introduced is formed at a center of the liquid charging cap.

* * * * *